United States Patent [19]
DeStefanis

[11] Patent Number: 5,346,394
[45] Date of Patent: Sep. 13, 1994

[54] MOLTEN WAX APPLICATOR

[76] Inventor: Mario P. DeStefanis, 10925 SW. Riverside Dr., Portland

[21] Appl. No.: 151,863

[22] Filed: Nov. 15, 1993

[51] Int. Cl.$^5$ ............................................. A61C 3/00
[52] U.S. Cl. ...................................................... 433/32
[58] Field of Search ................... 433/32; 219/236, 239, 219/385; 222/146.5; 401/1, 2; 392/385

[56] References Cited

U.S. PATENT DOCUMENTS

| | | | |
|---|---|---|---|
| 1,880,176 | 9/1932 | Harris | 433/32 |
| 2,243,400 | 5/1941 | Stack | 433/32 |
| 3,522,654 | 8/1970 | Schoelz | 433/32 |

FOREIGN PATENT DOCUMENTS 3314585  12/1983  Fed. Rep. of Germany ........ 433/32

*Primary Examiner*—Cary E. O'Connor
*Attorney, Agent, or Firm*—Eugene D. Farley

[57] ABSTRACT

A molten wax applicator for use in building up wax patterns and forms, particularly in dental applications. A hollow, heated stock provides a reservoir for holding molten wax. A nozzle having a wax-dispensing tip connects to the stock. A conduit through the nozzle interconnects the reservoir with the dispensing tip. A valve raceway intercepts the conduit. A valve incorporating resilient, polymeric conduit-sealing elements works in the raceway. A valve actuator with associated lock is connected to the valve for shifting it between open and closed positions permitting, in the open position, controlled dropwise or continuous flow of molten wax to the work.

13 Claims, 2 Drawing Sheets

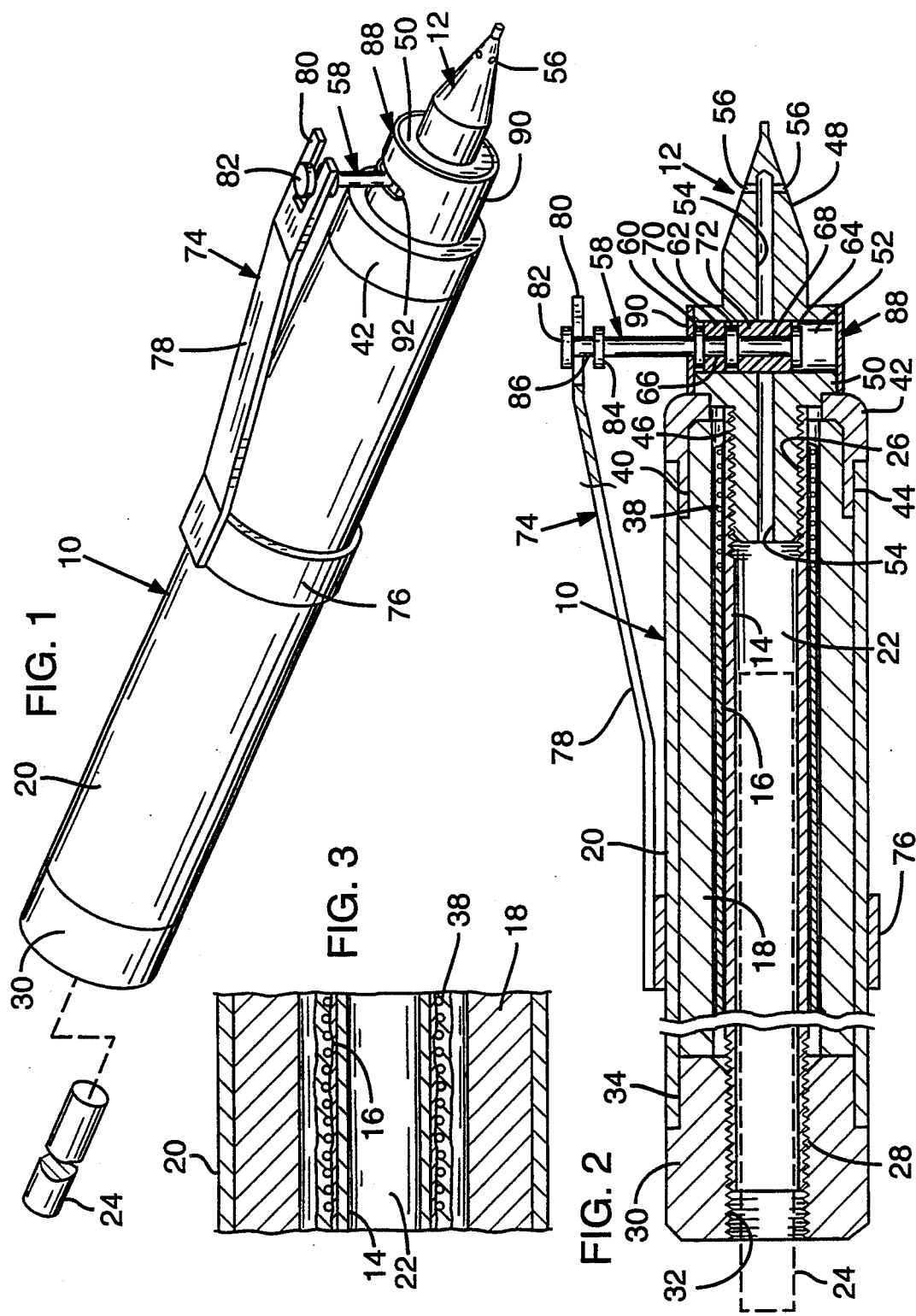

MOLTEN WAX APPLICATOR

This invention relates to molten wax applicators of the class employed for dispensing wax in controlled amounts in the fabrication of wax patterns used in dentistry and jewelry, and in the manufacture of various mechanical appliances such as jet engine vanes.

BACKGROUND OF THE INVENTION

In the past, wax patterns have been fabricated by the addition of small increments of molten wax to the main body of the pattern. In the construction of dental bridge work, inlays and crowns, for example, a dental instrument is heated over a flame and then touched to a bulk supply of wax. The molten wax thus deposited on the end of the instrument then is transported to, and placed on, the embryonic pattern. Building up a pattern in this manner is repetitive, tedious and enormously time consuming.

It has been proposed (Schoelz U.S. Pat. No. 3,522,654) to meet this problem by the provision of a pen-like waxing tool in which molten wax contained in a reservoir is discharged onto the wax pattern through a nozzle, continuously or incrementally. However, in the execution of this technique a serious and often fatal problem is presented by the fact that molten wax has the curious and unique property of seeping through flow control valves fabricated from metal, glass or ceramic parts, This is believed to be a surface tension phenomenon. Molten wax at atmospheric pressure will leak through a valve fabricated from metal components which is impervious to water at 50,000 psi. This property of molten wax destroys the utility of the implement, since it is impossible to control the flow of molten wax accurately.

It is the general purpose of the present invention to provide a molten wax applicator which is impervious to the flow of wax and leak proof when the applicator is in its closed or turned off mode.

It is a further important object of the present invention to provide a molten wax dispenser which is convenient to hold and operate and which has the capability of delivering molten wax drop-wise or continuously on demand, but which is leak-proof when not in use.

Further objects of the present invention are the provision of such an applicator in which the temperature of the molten wax can be controlled accurately, in which the quantity of molten wax dispensed can be controlled accurately, which compensates for expansion and contraction of associated valving components, which will withstand high temperatures, which is adaptable to the dispensing of molten wax in large or small amounts, which can be easily assembled, cleaned and serviced; and which is easily loaded with the feed wax.

It is still a further object of the invention to provide a molten wax applicator having a hot nozzle through which the wax is dispensed. The hot nozzle melts the surface of the embryonic pattern, ensuring complete fusion of the newly added wax increment to the pattern.

SUMMARY OF THE INVENTION

As noted, molten wax will seep through a valve including the most precisely machined metal valve components that have the capacity of stopping entirely the flow of water under enormous pressure. The present invention is predicated on the discovery that molten wax flow may be stopped entirely, and controlled precisely, by the application of a valving system including a polymeric material such as Teflon (polytetrafluoroethylene) as one of the valving surfaces. Thus such surfaces may be Teflon and metal, Teflon and glass, Teflon and ceramic and the like.

In its broad aspect, the molten wax applicator of my invention comprises a hollow stock providing a reservoir for holding molten wax. An electric or other suitable heating means in operative contact with the reservoir maintains the wax in molten condition.

Connected to the stock is a heat conductive (metal) nozzle having a wax-dispensing tip. A conduit through the nozzle interconnects the reservoir with the dispensing tip.

Valve means incorporating a conduit-sealing element of polymeric material controls the flow of molten wax through the conduit. A valve actuator connected to the valve means shifts it between open and closed positions.

All of the applicator components may be assembled in a tubular unit of convenient size which may be held comfortably, pen-like, in the hand for application of the wax increments to the pattern which is in process of formation.

THE DRAWINGS

FIG. 1 is a view in perspective of the molten wax applicator of the invention in its assembled condition.

FIG. 2 is a foreshortened view in longitudinal section of the applicator.

FIG. 3 is a fragmentary enlarged view in longitudinal section of a central portion of the applicator.

DETAILED DESCRIPTION OF A SPECIFIC EMBODIMENT OF THE INVENTION

Figure 4:
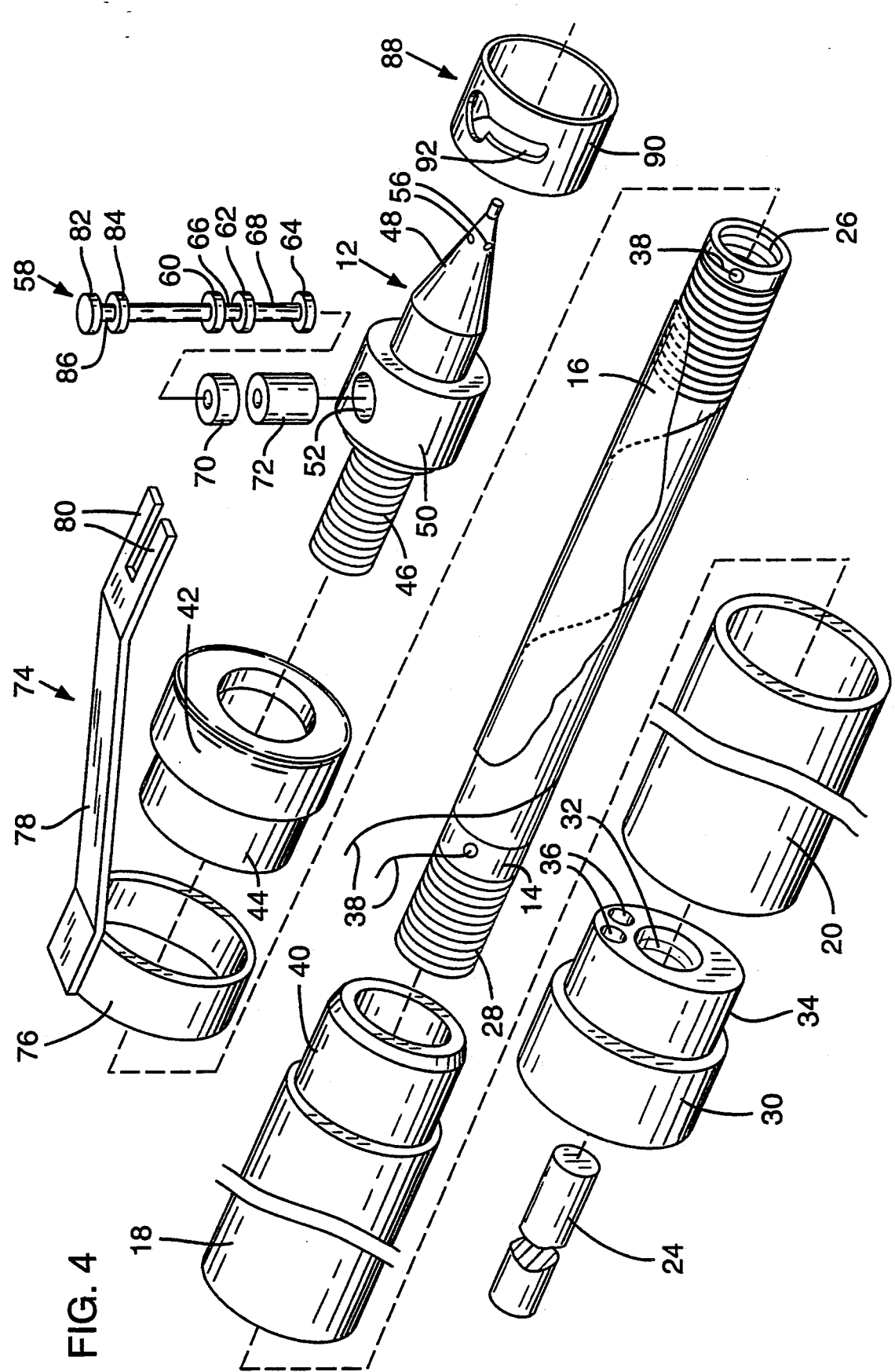
FIG. 4 is an exploded view of the applicator illustrating the component parts and their relation to each other.

As noted above, the molten wax applicator of my invention broadly comprises a stock or handle 10 to which is affixed a molten wax dispensing nozzle 12.

Stock 10 is dimensioned and contoured in the manner of a pen or other writing instrument. It is designed to be held and manipulated between the thumb and fingers in the manner of such an instrument. It comprises four tubular, concentrically-arranged components, a central tube 14, an electric heating element 16, an insulating jacket 18, and an external case 20.

Central tube 14 provides a reservoir 22 for a supply of molten wax. The wax in turn is available commercially in the form of a rod or "rope" 24. Various waxes may be employed, including candelilla wax, carnauba wax, or paraffin wax. All have melting points in the broad range of from 200° to 320° F.

Central tube 14 is fabricated from a thermally conductive, non-corrodable material such as copper, silver, brass or bronze. It extends almost entirely the entire length of stock 10. Its forward end 26 is internally threaded for the attachment of nozzle 12 and outwardly grooved in a spiral pattern for guiding and evenly spacing the electric heating element 38 which is mounted upon it. Its rearward end 28 is externally threaded for the attachment of a cap piece 30.

The latter element of the assembly has an internally threaded longitudinal bore 32 for attachment to central tube 14. It is open at its rear end for introduction of wax rope 24. Also, its forward end is externally stepped at 34 for the reception of the rearward end of case 20. It is constructed of a suitable constructional material, preferably of heat-resistant, molded plastic.

Rearward cap 30 is formed with a pair of separated wire holes 36 for the reception of the electric wires which service the heating unit and by means of which the leading end of wax rope 24 is heated and melted.

This heating unit, illustrated generally at 16, comprises a Nichrome or other electric resistance wire 38 embedded in a suitable insulating matrix. It is to be noted that the heating element, the wire, is arranged to heat the thermally conductive central tube preferentially in the forward portion of the latter, FIG. 2. As a result, during operation of the appliance the leading end only of the wax rope feed is melted. It supplies molten wax selectively to the forward portion of reservoir 22.

The trailing portion of wax rope 24 remains solid and serves as a plug for retaining the molten wax in the reservoir. There thus is provided a means for continuously feeding the tool with wax during its operation. Wax may be continuously introduced via the open end 32 of cap piece 30 and the communicating bore of center tube 14.

The assembly of central tube 14 and heating element 16 thus provided is received in an insulating jacket 18. This component of the tool may be fabricated from fiberglass or other suitable thermally and electrically insulating material. It possesses a forward chamfered end segment of reduced cross section 40, which mounts a forward cap piece 42.

Like rearward cap piece 30, forward cap piece 42 preferably is fabricated from a heat resistant molded plastic such as Teflon. It has a longitudinal bore extending its entire length and an external stepped segment 44 on which is mounted the leading end of outer case 20.

Case 20 preferably comprises simply a tube of hard, durable plastic contoured to be held pen-like between the fingers. As noted, it is mounted on the opposed stepped segments of rearward cap piece 30 and forward cap piece 42.

Nozzle 12 is fabricated from a suitable heat conductive, corrosion-resistant material of the group consisting of copper, silver, brass and bronze. It has an externally threaded rearward portion 46 by means of which it is attached to the leading end of center tube 14. It also has a dispensing tip 48 by means of which molten wax is applied to the pattern form being built up.

The center section 50 of nozzle 12 is of enlarged diameter and has an enlarged transverse bore 52.

A longitudinal bore 54 terminating externally in dispensing ports 56 intercepts transverse bore 52. At its inner end it communicates with reservoir 22 and provides a means for transporting the molten wax by gravity to the dispensing tip 48 of the nozzle.

Transverse bore 52 forms the raceway for reciprocating valve means by means of which the molten wax is fed to the dispensing tip of the nozzle.

As illustrated particularly in FIG. 4, the valve means comprises a spool-type valve including a valve stem 58. The valve stem includes three spaced lands 60, 62, 64 defining two spaced grooves 66, 68.

Central land 62 is positioned to register with conduit 54 through the nozzle, thereby continuing the conduit in the open position of the valve.

Grooves 66, 68 are dimensioned and contoured to receive cylindrical washers 70, 72 in valve-sealing relation. These elements of the assembly are critical to the successful operation of the applicator.

As noted above, molten wax has the unique capability, of working its way through the most precisely machined valve having metal valving components. Even though such a valve has the capability of sealing off the flow of water under pressures of the order of 50,000 psi, it is subject to permeation and leakage under the gravity flow of molten wax.

Accordingly, the material of which washers 70, 72 are fabricated is of critical importance in determining the successful operation of the herein described appliance. Not only must the material generate a leak-proof relationship between the valve components, it also must be stable against the corrosive influence of molten wax, and it must retain these desirable properties over long operating intervals at high temperatures. Furthermore, it should be resistant to wear and self-lubricating.

I have discovered that the above noted essential qualities are demonstrated by plastic substances which may be characterized as resilient polymeric materials which are chemically resistant to the action of hot molten wax and which melt at a temperature of from 150°–480° F., preferably from 180°–240° F. Such materials comprise the group consisting of The polymeric fluorocarbons
The polymeric silicones
The polymeric fluorosilicones An illustrative polymeric silicone is polydimethyl methyl vinyl poly silicone.

The polymeric fluorocarbons are especially suitable. Illustrative ones are:
polytetrafluoroethylene (Teflon)
polychloro trifluoro ethylene
polymeric fluorinated ethylene propylene When mounted on valve stem 58 in the manner illustrated in FIGS. 1 and 4, washers 70, 72 made of the above-described polymeric materials provide the metal-plastic meeting surfaces required to achieve the purposes of the invention.

Actuator means indicated generally at 74 adjust the valve between open and closed positions.

In the illustrated form of the invention the actuator means comprises a retaining band 76 which mounts the actuator on case 20, and a resilient lever arm or spring arm 78 having a notched terminal portion 80.

In addition to lands 60, 62, 64, valve stem 58 has a pair of spaced terminal lands 82, 84. These provide a groove 86 dimensioned to receive the slotted end of spring arm 78.

Locking means indicated generally at 88 releasably retains the valve in its assembled position.

A locking sleeve or stop 90 having a keyhole slot 92 is mounted rotatably on enlarged segment 50 of nozzle 12. Valve stem 58 extends through and works in keyhole slot 92. Radial adjustment of sleeve 90 to place the enlarged portion of keyhole slot 92 in operative position relative to valve stem 58 adjusts the valve to its disassemblable position. Radial adjustment of the sleeve to place the restricted portion of slot 92 in operative position relative to valve stem groove 86 adjusts the valve to its operative position in which land 60 bottoms out against sleeve 90 in the closed position of the valve.

OPERATION

The operation of the herein described molten wax applicator is as follows:

With the valve in its closed position, a supply of wax rope 24 is fed into the hollow barrel of center tube 14. When fully inserted, it registers with the heating element of resistance wire 38. Energization of the latter results in melting the wax selectively in the forward end of the tube. This forms a pool of molten wax in reservoir 22. Escape of molten wax through the open rear end of the tube is prevented by the presence of a solid plug of unmelted wax.

In use, the applicator is held in a vertically inclined position with nozzle 12 pointed downwardly. Depression of spring lever 74 will bring land 62 of valve stem 58 into registry with conduit 54. Since land 62 is of restricted diameter, it provides a continuous channel with conduit 54 so that molten wax can flow outwardly through dispensing ports 56 and thence to the work.

Permitting spring arm 78 to return to its FIG. 2 position results in sealing off the conduit and interrupting the flow of wax. Surface contact with washers 70, 72 at all times seals off the working areas of raceway 52.

Adjustment of valve lock 88 releasably holds the valve in its assembled condition.

Having thus described in detail a preferred embodiment of the invention, it will be apparent to those skilled in the art that various changes may be made without altering the inventive concepts and principles embodied. The present embodiment therefore is to be considered in all respects as illustrative and not restrictive, the scope of the invention being indicated by the appended claims.

I claim:

1. A molten wax applicator comprising:
   a) a hollow stock providing a reservoir for holding molten wax,
   b) heating means in operative contact with the reservoir for maintaining the wax in molten condition,
   c) connected to the stock a heat conductive nozzle having a wax-dispensing tip,
   d) a conduit through the nozzle interconnecting the reservoir with the dispensing tip, and
   e) positioned in the tip for controlling the flow of molten wax through the conduit, valve means incorporating as a conduit-sealing component a component fabricated from a resilient polymeric material which is chemically resistant to the action of hot molten wax and which melts at a temperature of from 150°–480° F.

2. The applicator of claim 1 wherein the polymeric material has a melting point of from 180°–240° F.

3. The applicator of claim 1 wherein the polymeric material is a member of the group consisting of the polymeric fluorocarbons, the polymeric silicones, and the polymeric fluorosilicones.

4. The applicator of claim 1 wherein the polymeric material is polytetrafluoroethylene (Teflon).

5. The applicator of claim 1 wherein the polymeric material is polychloro trifluoro ethylene.

6. The applicator of claim 1 wherein the polymeric material is polymeric fluorinated ethylene propylene.

7. The applicator of claim 1 wherein the polymeric material is polydimethyl methyl vinyl poly silicone.

8. A molten wax applicator comprising:
   a) a hollow stock providing a reservoir for holding molten wax;
   b) heating means in operative contact with the reservoir for maintaining a quantity of wax in molten condition,
   c) connected to the stock a heat conductive nozzle having a wax-dispensing tip,
   d) a conduit through the nozzle interconnecting the reservoir with the dispensing tip,
   e) a valve raceway intercepting the conduit,
   f) valve means incorporating a polytetrafluoroethylene (Teflon) conduit-sealing element working in the raceway, and
   g) valve actuator means connected to the valve means for adjusting it between open and closed positions.

9. The molten wax applicator of claim 8 wherein the nozzle is fabricated from a heat conductive metal of the group consisting of copper, silver, brass and bronze.

10. The molten wax applicator of claim 8 wherein the stock comprises in concentric arrangement a heat-conductive metal tube connected to the nozzle and adapted to contain a quantity of wax, an electric heating element receiving the tube, and a pen-shaped, thermally-insulated case receiving the heating element and tube.

11. The molten wax applicator of claim 10 wherein the stock is provided with a feed opening adapted to receive a length of solid wax rope positioned to form a plug which seals off the reservoir.

12. The molten wax applicator of claim 8 wherein the valve means comprises reciprocating valve means including a valve stem provided with three spaced lands defining two spaced grooves, the central land being positioned and dimensioned to register with the conduit in the open position of the valve and thereby provide a channel for passage of molten wax through the conduit,
   in each groove Teflon washer means positioned and dimensioned for closing off the conduit in the closed position of the valve and sealing the raceway against leakage in both the open and closed positions of the valve.

13. The molten wax applicator of claim 12 wherein the valve actuator means comprises spring pressed lever means connected to the valve stem component of the valve means.

* * * * *